United States Patent
Lafferty et al.

(10) Patent No.: US 8,500,677 B2
(45) Date of Patent: Aug. 6, 2013

(54) POWER INJECTOR WITH FLOW RATE ASSESSMENT

(75) Inventors: Sean B. Lafferty, Taylor Mill, KY (US); Gary S. Wagner, Independence, KY (US)

(73) Assignee: Mallinckrodt LLC, Hazelwood, MO (US)

( * ) Notice: Subject to any disclaimer, the term of this patent is extended or adjusted under 35 U.S.C. 154(b) by 68 days.

(21) Appl. No.: 12/742,943

(22) PCT Filed: Nov. 19, 2008

(86) PCT No.: PCT/US2008/083997
§ 371 (c)(1),
(2), (4) Date: May 14, 2010

(87) PCT Pub. No.: WO2009/067492
PCT Pub. Date: May 28, 2009

(65) Prior Publication Data
US 2010/0274182 A1 Oct. 28, 2010

Related U.S. Application Data

(60) Provisional application No. 60/989,145, filed on Nov. 20, 2007.

(51) Int. Cl.
*A61M 31/00* (2006.01)
(52) U.S. Cl.
USPC .......................................................... 604/67
(58) Field of Classification Search
USPC ............................. 604/65–71, 118, 121, 151
See application file for complete search history.

(56) References Cited

U.S. PATENT DOCUMENTS

| | | | | |
|---|---|---|---|---|
| 4,534,756 A | * | 8/1985 | Nelson | 604/505 |
| 4,854,324 A | * | 8/1989 | Hirschman et al. | 600/432 |
| 4,959,050 A | * | 9/1990 | Bobo, Jr. | 604/505 |
| 5,840,026 A | * | 11/1998 | Uber et al. | 600/431 |
| 5,868,710 A | * | 2/1999 | Battiato et al. | 604/123 |
| 5,925,022 A | * | 7/1999 | Battiato et al. | 604/208 |
| 6,004,292 A | * | 12/1999 | Battiato et al. | 604/123 |
| 6,159,183 A | * | 12/2000 | Neer et al. | 604/189 |
| 6,470,889 B1 | * | 10/2002 | Bae et al. | 604/28 |
| 6,635,030 B1 | * | 10/2003 | Bae et al. | 604/131 |
| 7,044,933 B2 | * | 5/2006 | VanDiver et al. | 604/151 |
| 7,753,885 B2 | * | 7/2010 | Duchon et al. | 604/151 |
| 7,854,726 B2 | * | 12/2010 | Fago et al. | 604/187 |
| 2002/0016567 A1 | | 2/2002 | Hochman et al. | |
| 2002/0198496 A1 | | 12/2002 | Duchon et al. | |
| 2004/0133165 A1 | * | 7/2004 | Duchon et al. | 604/151 |
| 2006/0079768 A1 | * | 4/2006 | Small et al. | 600/432 |

(Continued)

FOREIGN PATENT DOCUMENTS

EP 1681069 7/2006
WO WO 2005107419 A2 * 11/2005

*Primary Examiner* — Nicholas Lucchesi
*Assistant Examiner* — Diva K Chander
(74) *Attorney, Agent, or Firm* — Marsh Fischmann & Breyfogle LLP

(57) ABSTRACT

A flow rate assessment protocol (140) that may be utilized by a power injector (10) is disclosed. This flow rate assessment protocol (140) monitors a flow rate (156) during execution of a medical fluid delivery protocol (154). This monitored flow rate is compared with a target flow rate (158). A comparative output of this monitored flow rate and target flow rate is displayed (160), for instance on a graphical user interface (11).

21 Claims, 11 Drawing Sheets

U.S. PATENT DOCUMENTS

| | | |
|---|---|---|
| 2006/0079842 A1* | 4/2006 | Small et al. .................. 604/151 |
| 2006/0079843 A1* | 4/2006 | Brooks et al. ................ 604/151 |
| 2006/0122555 A1* | 6/2006 | Hochman ....................... 604/67 |
| 2007/0083152 A1* | 4/2007 | Williams et al. ............... 604/65 |
| 2007/0093712 A1 | 4/2007 | Nemoto et al. |
| 2007/0100282 A1* | 5/2007 | Small et al. .................. 604/151 |
| 2007/0106153 A1* | 5/2007 | Neer et al. .................... 600/432 |
| 2008/0108943 A1* | 5/2008 | Wagner ......................... 604/151 |
| 2010/0249704 A1* | 9/2010 | Wagner ......................... 604/121 |
| 2010/0293496 A1* | 11/2010 | Lafferty et al. .............. 715/772 |

* cited by examiner

POWER INJECTOR WITH FLOW RATE ASSESSMENT

CROSS-REFERENCE TO RELATED APPLICATIONS

This patent application is a U.S. National Stage of PCT/US08/083997, filed 19 Nov. 2008, which claims priority to and is a non-provisional application of U.S. Provisional Patent Application Ser. No. 60/989,145, that is entitled "POWER INJECTOR WITH FLOW RATE ASSESSMENT," and that was filed on Nov. 20, 2007.

FIELD OF THE INVENTION

The present invention generally relates to the field of fluid delivery and, more particularly, to providing a comparative display of a target flow rate and an actual flow rate.

BACKGROUND

Various medical procedures require that one as or more fluids be injected into the patient. Medical imaging procedures oftentimes involve the injection of a contrast media into the patient, possibly along with saline or other fluids. Other medical procedures involve injecting one or more fluids into a patient for therapeutic purposes. Power injectors may be used for these types of applications.

A power injector generally includes what is commonly referred to as a powerhead. One or more syringes may be mounted to the powerhead in various manners (e.g., detachably; rear-loading; front-loading; side-loading). Each syringe typically includes what may be characterized as a syringe plunger, piston, or the like. Each such syringe plunger is appropriately interconnected with an appropriate syringe plunger driver that is incorporated into the powerhead, such that operation of the syringe plunger driver axially advances the associated syringe plunger. One typical syringe plunger driver is in the form of a ram that is mounted on a threaded lead or drive screw. Rotation of the drive screw in one rotational direction advances the associated ram in one axial direction, while rotation of the drive screw in the opposite rotational direction advances the associated ram in the opposite axial direction.

At least some commercially available power injectors utilize a pressure limit. A user may utilize a data entry device to enter a desired value for the pressure limit. A pressure is monitored during execution of an injection procedure. In the event that this monitored pressure reaches or exceeds an associated pressure limit, an alert may be issued to appropriate personnel. This alert may appear on a graphical user interface associated with the power injector.

SUMMARY

A first aspect of the present invention is embodied by a method of operation for a medical fluid delivery system. Fluid is discharged from the medical fluid delivery system (e.g., to a fluid target), and a first output is displayed. This first output is in the form of a relationship between a target flow rate and a current flow rate for the fluid being discharged from the medical fluid delivery system.

A second aspect of the present invention is embodied by a power injector. This power injector includes a powerhead, a syringe plunger driver, a graphical user interface, and control logic. This control logic is configured to execute a medical fluid delivery protocol, as well as to present a first output on the first graphical user interface. This first output is in the form of a relationship between a target flow rate associated with the medical fluid delivery protocol and a current flow rate that exists during execution of the medical fluid delivery protocol.

Various refinements exist of the features noted in relation to each of the above-noted first and second aspects of the present invention. Further features may also be incorporated in each of the above-noted first and second aspects of the present invention as well. These refinements and additional features may exist individually or in any combination in relation to each of the first and second aspects. That is, each of the following features that will be discussed is not required to be used with any other feature or combination of features unless otherwise specified.

Fluid may be discharged to a fluid target in any appropriate manner, for instance using a power injector. In one embodiment, fluid is injected into a fluid target. Any such fluid target may be of any appropriate size, shape, configuration, and/or type. In one embodiment, the fluid target is a patient of any appropriate type (e.g., a human, an animal).

Fluid may be discharged to a fluid target in accordance with the target flow rate. One or more conditions may impact the ability of the fluid to actually be discharged in accordance with the target flow rate, for instance the existence of a partial or total occlusion/obstruction in the flowpath leading to a fluid target. Presenting a comparative output of the target flow rate and current flow rate may provide valuable information to a user or operator, for instance in the case where fluid is being injected into a patient for an imaging application.

The first output may be displayed on at least one graphical user interface, at one or more locations, or both. In one embodiment, the first output is displayed on a graphical user interface associated with a power injector (e.g., on a powerhead, on a remote console, or both). The first output may be displayed only when at least a certain variance exists between the current flow rate and the target flow rate (e.g., a certain flow rate condition). Another option is to continually display the first output during the delivery of fluid to a fluid target.

The first output may compare the current flow rate with the target flow rate in any appropriate manner. The first output may be in the form of displaying a magnitude of both the current flow rate and the target flow rate. In one embodiment, the magnitude of each of the current flow rate and the target flow rate are numerically presented (e.g., "x" milliliters/second). In another embodiment, the magnitude of each of the current flow rate and the target flow rate are graphically presented in any appropriate manner (e.g., on a common "flow rate meter"; on separate "flow rate meters"). The first output may be in the form of an expression of the current flow rate as a percentage of the target flow rate (e.g., 97%). The first output may also be in the form of a differential between the current flow rate and the target flow rate (e.g., −2 milliliters/second). In one embodiment, the current flow rate is not allowed to exceed the target flow rate. Although this may be preferred in at least some instances, it may not be required in all instances. If the actual flow rate were allowed to be greater than the target flow rate, whether the current flow rate is greater than or less than the target flow rate may be expressed by incorporating an appropriate sign with the first output (e.g., a positive sign may indicate that the current flow rate is greater than the target flow rate, while a negative sign may indicate that the current flow rate is less than the target flow rate, or vice versa).

Any appropriate action may be undertaken if a certain variance exists between the current flow rate and the target flow rate. In one embodiment, a message may be displayed and/or one or more alerts may be issued to indicate that the discharge of fluid from a medical fluid delivery system (e.g., to a fluid target) is not in accordance with the corresponding target flow rate, that the current flow rate is outside of an acceptable/selected flow rate variance from the target flow rate, that a certain flow rate condition exists, or the like. In one embodiment, the discharge of medical fluid from a medical fluid delivery system (e.g., a power injector) may be changed in at least some manner (e.g., suspended, terminated). A flow rate variance that may trigger the issuance of a message and/or at least one alert may be the same as or different from a flow rate variance that may trigger making at least some type of change in the discharge of medical fluid from a medical fluid delivery system (e.g., a power injector). For instance, a smaller flow rate variance may be utilized to trigger the issuance of a message and/or at least one alert, compared to a larger flow rate variance that may be utilized to trigger a suspension or termination of the discharge of medical fluid from a medical fluid delivery system (e.g., a power injector).

A flow rate variance that may trigger the issuance of a message and/or at least one alert and/or that may trigger making at least some type of change in the discharge of medical fluid from a medical fluid delivery system (e.g., a power injector) may be only if the current flow rate is in excess of the target flow rate, may be only if the current flow rate is less than the target flow rate, or may be if the current flow rate is greater than or less than the target flow rate. A flow rate variance that triggers the issuance of a message and/or at least one alert, as well as a flow rate variance that triggers at least some type of change in the discharge of medical fluid from a medical fluid delivery system (e.g., a power injector) (e.g., a suspension or termination of a medical fluid delivery protocol) may be inputtable/selectable in any appropriate manner (e.g., through a data entry device such as a keyboard, mouse, touch pad, track ball, touch screen display, soft key display or the like, that may be operatively interconnected with control logic). In one embodiment, a prompt is issued on at least one graphical user interface for a user/operator to input at least one flow rate variance or flow rate condition.

Any power injector that may be utilized may be of any appropriate size, shape, configuration, and/or type. Any such power injector may utilize one or more syringe plunger drivers of any appropriate size, shape, configuration, and/or type, where each such syringe plunger driver is capable of at least bi-directional movement (e.g., a movement in a first direction for discharging fluid; a movement in a second direction for accommodating a loading of fluid or so as return to a position for a subsequent fluid discharge operation), and where each such syringe plunger driver may interact with its corresponding syringe plunger in any appropriate manner (e.g., by mechanical contact; by an appropriate coupling (mechanical or otherwise)) so as to be able to advance the syringe plunger in at least one direction (e.g. to discharge fluid). Any such power injector may be used for any appropriate application where the delivery of one or more fluids is desired, including without limitation any appropriate medical application (e.g., computed tomography or CT imaging; magnetic resonance imaging or MRI; SPECT imaging; PET imaging; X-ray imaging; angiographic imaging; optical imaging; ultrasound imaging). Any such power injector may be used in conjunction with any component or combination of components, such as an appropriate imaging system (e.g., a CT scanner). For instance, information could be conveyed between any such power injector and one or more other components (e.g., scan delay information, injection start signal, injection rate). Any appropriate number of syringes may be integrated with any such power injector in any appropriate manner (e.g., detachably; front-loaded; rear-loaded; side-loaded), any appropriate fluid may be discharged from a given syringe of any such power injector (e.g., contrast media, a radiopharmaceutical, saline, and any combination thereof), and any appropriate fluid may be discharged from a multiple syringe power injector configuration in any appropriate manner (e.g., sequentially, simultaneously), or any combination thereof. In one embodiment, fluid discharged from a syringe by operation of the power injector is directed into a conduit, where this conduit is fluidly interconnected with the syringe in any appropriate manner and directs fluid to a desired location (e.g., to a patient).

DETAILED DESCRIPTION

Figure 1:
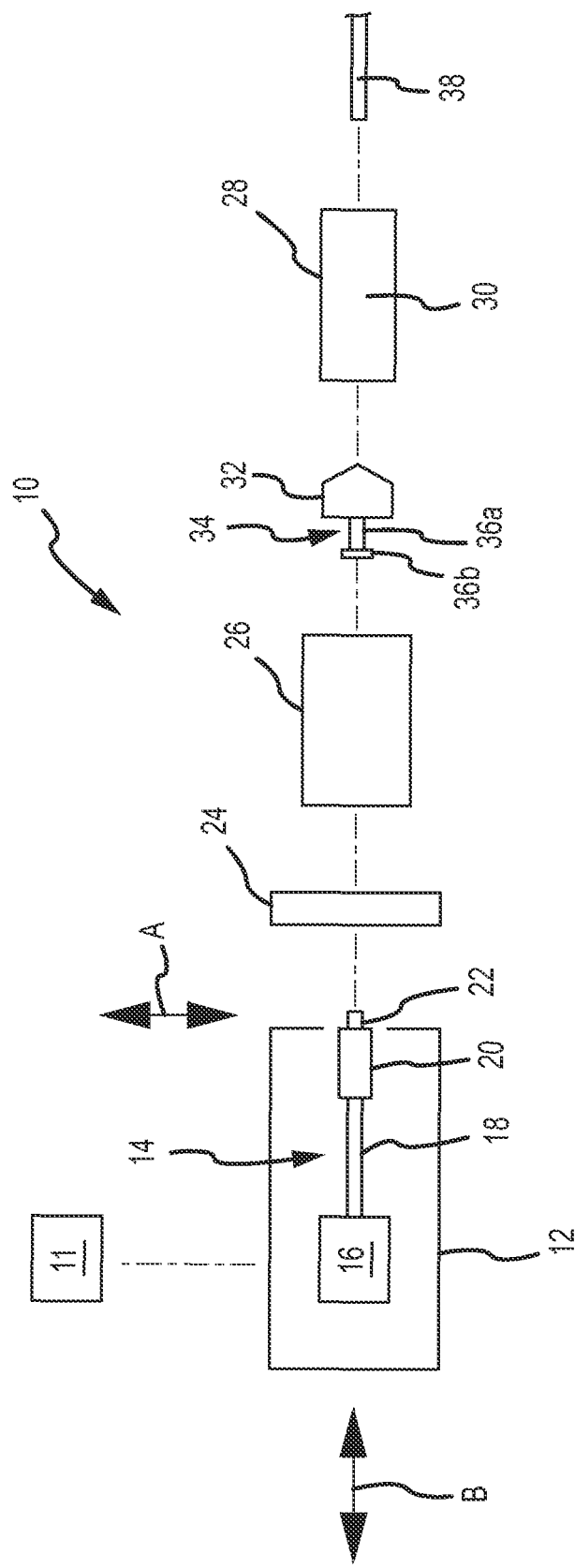
FIG. 1 is a schematic of one embodiment of a power injector.

FIG. 1 presents a schematic of one embodiment of a power injector 10 having a powerhead 12. One or more graphical user interfaces or GUIs 11 may be associated with the powerhead 12. Each GUI 11: 1) may be of any appropriate size, shape, configuration, and/or type; 2) may be operatively interconnected with the powerhead 12 in any appropriate manner; 3) may be disposed at any appropriate location; 4) may be configured to provide one or any combination of the following functions; controlling one or more aspects of the operation of the power injector 10; inputting/editing one or more parameters associated with the operation of the power injector 10; and displaying appropriate information (e.g., associated with the operation of the power injector 10); or 5) any combination of the foregoing. Any appropriate number of GUIs 11 may be utilized. In one embodiment, the power to injector 10 includes a GUI 11 that is incorporated by a console that is separate from but which communicates with the powerhead 12. In another embodiment, the power injector 10 includes a GUI 11 that is part of the powerhead 12. In yet another embodiment, the power injector 10 utilizes one GUI 11 on a separate console that communicates with the powerhead 12, and also utilizes another GUI 11 that is on the powerhead 12. Each GUI 11 could provide the same functionality or set of functionalities, or the GUIs 11 may differ in at least some respect in relation to their respective functionalities.

A syringe 28 may be installed on this powerhead 12 and may be considered to be part of the power injector 10. Some injection procedures may result in a relatively high pressure being generated within the syringe 28. In this regard, it may be desirable to dispose the syringe 28 within a pressure jacket 26. The pressure jacket 26 is typically installed on the powerhead 12, followed by disposing the syringe 28 within the pressure jacket 26. The same pressure jacket 26 will typically remain installed on the powerhead 12, as various syringes 28 are positioned within and removed from the pressure jacket 26 for multiple injection procedures. The power injector 10 may eliminate the pressure jacket 26 if the power injector 10 is configured/utilized for low-pressure injections. In any case, fluid discharged from the syringe 28 may be directed into a conduit 38 of any appropriate size, shape, configuration, and/or type, which may be fluidly interconnected with the syringe 28 in any appropriate manner, and which may direct fluid to any appropriate location (e.g., to a patient).

The powerhead 12 includes a syringe plunger drive assembly or syringe plunger driver 14 that interacts (e.g., interfaces) with the syringe 28 to discharge fluid from the syringe 28. This syringe plunger drive assembly 14 includes a drive source 16 (e.g., a motor of any appropriate size, shape, configuration, and/or type, optional gearing, and the like) that powers a drive output 18 (e.g., a rotatable drive screw). A ram 20 may be advanced along an appropriate path (e.g., axial) by the drive output 18. The ram 20 may include a coupler 22 for interfacing with a corresponding portion of the syringe 28 in a manner that will be discussed below.

The syringe 28 includes a plunger or piston 32 that is movably disposed within a syringe barrel 30 (e.g., for axial reciprocation along an axis coinciding with the double-headed arrow B). The plunger 32 may include a coupler 34. This syringe plunger coupler 34 may interface or interact with the ram coupler 22 to allow the syringe plunger drive assembly 14 to retract the syringe plunger 32 within the syringe barrel 30. The syringe plunger coupler 34 may be in the form of a shaft 36a that extends from a body of the syringe plunger 32, together with a head or button 36b. However, the syringe plunger coupler 34 may be of any appropriate size, shape, configuration, and/or type.

Generally, the syringe plunger drive assembly 14 may interact with each syringe plunger 32 of the power injector 10 in any appropriate manner (e.g., by mechanical contact; by an appropriate coupling (mechanical or otherwise)) so as to be able to move or advance the syringe plunger 32 in at least one direction (e.g., to discharge fluid from the corresponding syringe 28). That is, although the syringe plunger drive assembly 14 may be capable of bi-directional motion (e.g., via operation of the same drive source 16), the power injector 10 may be configured such that the operation of the syringe plunger drive assembly 14 actually only moves each syringe plunger 32 being used by the power injector 10 in only one direction. However, the syringe plunger drive assembly 14 may be configured to interact with each syringe plunger 32 being used by the power injector 10 so as to be able to move each such syringe plunger 32 in each of two different directions (e.g. in different directions along a common axial path).

Retraction of the syringe plunger 32 may be utilized to accommodate a loading of fluid into the syringe barrel 30 for a subsequent injection or discharge, may be utilized to actually draw fluid into the syringe barrel 30 for a subsequent injection or discharge, or for any other appropriate purpose. Certain configurations may not require that the syringe plunger drive assembly 14 be able to retract the syringe plunger 32, in which case the ram coupler 22 and syringe plunger coupler 34 may not be required. In this case, the syringe plunger drive assembly 14 may be retracted for purposes of executing another fluid delivery operation (e.g., after another pre-filled syringe 28 has been installed). Even when a ram coupler 22 and syringe plunger coupler 34 are utilized, it may such that these components may or may not be coupled when the ram 20 advances the syringe plunger 32 to discharge fluid from the syringe 28 (e.g., the ram 20 may simply "push on" the syringe plunger coupler 34 or on a proximal end of the syringe plunger 32). Any single motion or combination of motions in any appropriate dimension or combination of dimensions may be utilized to dispose the ram coupler 22 and syringe plunger coupler 34 in a coupled state or condition, to dispose the ram coupler 22 and syringe plunger coupler 34 in an un-coupled state or condition, or both.

The syringe 28 may be installed on the powerhead 12 in any appropriate manner. For instance, the syringe 28 could be configured to be installed directly on the powerhead 12. In the illustrated embodiment, a housing 24 is appropriately mounted on the powerhead 12 to provide an interface between the syringe 28 and the powerhead 12. This housing 24 may be in the form of an adapter to which one or more configurations of syringes 28 may be installed, and where at least one configuration for a syringe 28 could be installed directly on the powerhead 12 without using any such adapter. The housing 24 may also be in the form of a faceplate to which one or more configurations of syringes 28 may be installed. In this case, it may be such that a faceplate is required to install a syringe 28 on the powerhead 12—the syringe 28 could not be installed on the powerhead 12 without the faceplate. When a pressure jacket 26 is being used, it may be installed on the powerhead 12 in the various manners discussed herein in relation to the syringe 28, and the syringe 28 will then thereafter be installed in the pressure jacket 26.

The housing 24 may be mounted on and remain in a fixed position relative to the powerhead 12 when installing a syringe 28. Another option is to movably interconnect the housing 24 and the powerhead 12 to accommodate installing a syringe 28. For instance, the housing 24 may move within a plane that contains the double-headed arrow A to provide one or more of coupled state or condition and an un-coupled state or condition between the ram coupler 22 and the syringe plunger coupler 34.

Figure 2A:
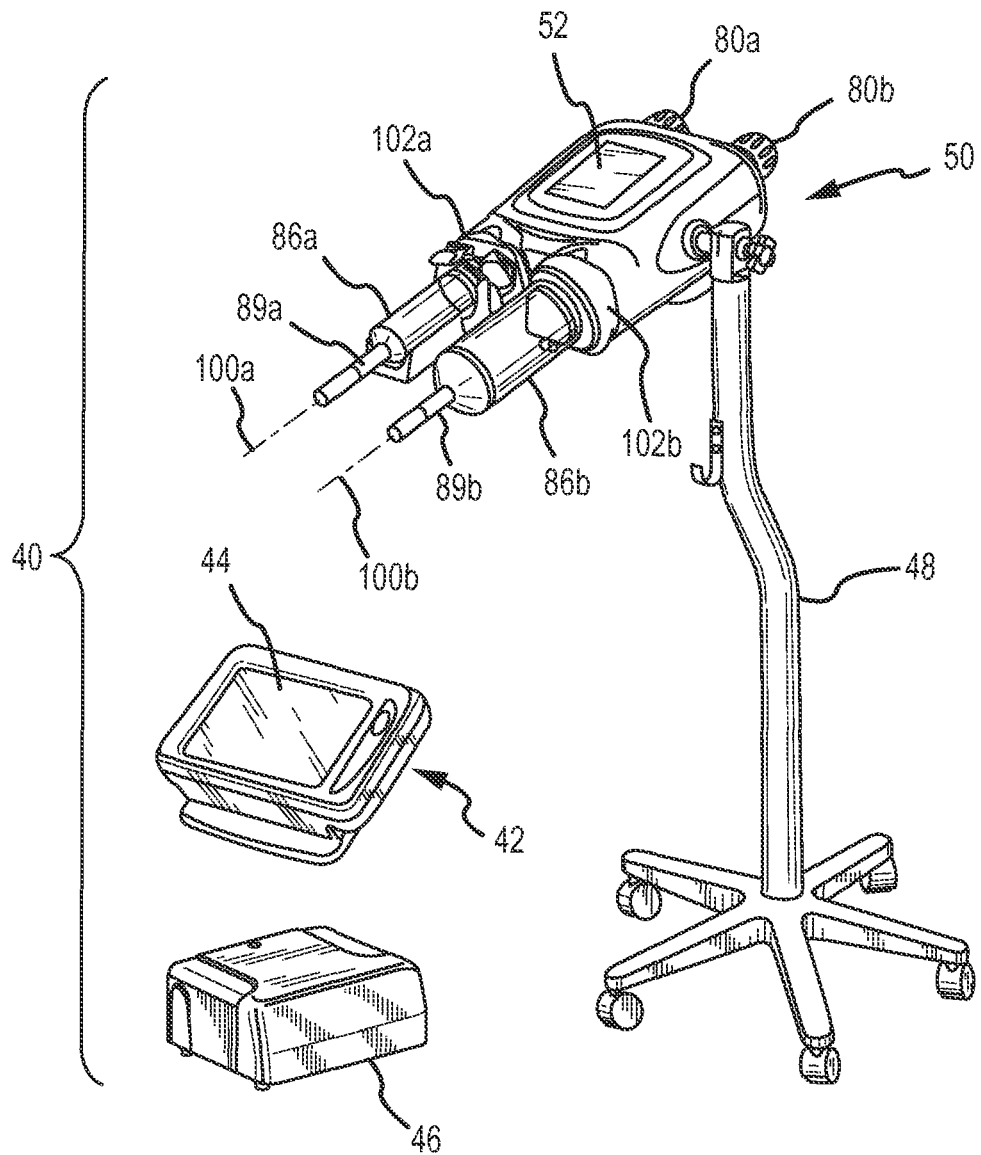
FIG. 2A is a perspective view of one embodiment of a portable stand-mounted, dual-head power injector.

One particular power injector configuration is illustrated in FIG. 2A, is identified by a reference numeral 40, and is at least generally in accordance with the power injector 10 of FIG. 1. The power injector 40 includes a powerhead 50 that is mounted on a portable stand 48. A pair of syringes 86a, 86b for the power injector 40 are mounted on the powerhead 50. Fluid may be discharged from the syringes 86a, 86b during operation of the power injector 40.

The portable stand 48 may be of any appropriate size, shape, configuration, and/or type. Wheels, rollers, casters, or the like may be utilized to make the stand 48 portable. The powerhead 50 could be maintained in a fixed position relative to the portable stand 48. However, it may be desirable to allow the position of the powerhead 50 to be adjustable relative to the portable stand 48 in at least some manner. For instance, it may be desirable to have the powerhead 50 in one position relative to the portable stand 48 when loading fluid into one or more of the syringes 86*a*, 86*b*, and to have the powerhead 50 in a different position relative to the portable stand 48 for performance of an injection procedure. In this regard, the powerhead 50 may be movably interconnected with the portable stand 48 in any appropriate manner (e.g., such that the powerhead 50 may be pivoted through at least a certain range of motion, and thereafter maintained in the desired position).

It should be appreciated that the powerhead 50 could be supported in any appropriate manner for providing fluid. For instance, instead of being mounted on a portable structure, the powerhead 50 could be interconnected with a support assembly, that in turn is mounted to an appropriate structure (e.g., ceiling, wall, floor). Any support assembly for the powerhead 50 may be positionally adjustable in at least some respect (e.g., by having one or more support sections that may be repositioned relative to one more other support sections), or may be maintained in a fixed position. Moreover, the powerhead 50 may be integrated with any such support assembly so as to either be maintained in a fixed position or so as to be adjustable relative the support assembly.

The powerhead 50 includes a graphical user interface or GUI 52. This GUI 52 may be configured to provide one or any combination of the following functions: controlling one or more aspects of the operation of the power injector 40; inputting/editing one or more parameters associated with the operation of the power injector 40; and displaying appropriate information (e.g., associated with the operation of the power injector 40). The power injector 40 may also include a console 42 and powerpack 46 that each may be in communication with the powerhead 50 in any appropriate manner (e.g., via one or more cables), that may be placed on a table or mounted on an electronics rack in an examination room or at any other appropriate location, or both. The powerpack 46 may include one or more of the following and in any appropriate combination: a power supply for the injector 40; interface circuitry for providing communication between the console 42 and powerhead 50; circuitry for permitting connection of the power injector 40 to remote units such as remote consoles, remote hand or foot control switches, or other original equipment manufacturer (OEM) remote control connections (e.g., to allow for the operation of power injector 40 to be synchronized with the x-ray exposure of an imaging system); and any other appropriate componentry. The console 42 may include a touch screen display 44, which in turn may provide one or more of the following functions and in any appropriate combination: allowing an operator to remotely control one or more aspects of the operation of the power injector 40; allowing an operator to enter/edit one or more parameters associated with the operation of the power injector 40; allowing an operator to specify and store programs for automated operation of the power injector 40 (which can later be automatically executed by the power injector 40 upon initiation by the operator); and displaying any appropriate information relation to the power injector 40 and including any aspect of its operation.

Figure 2B:
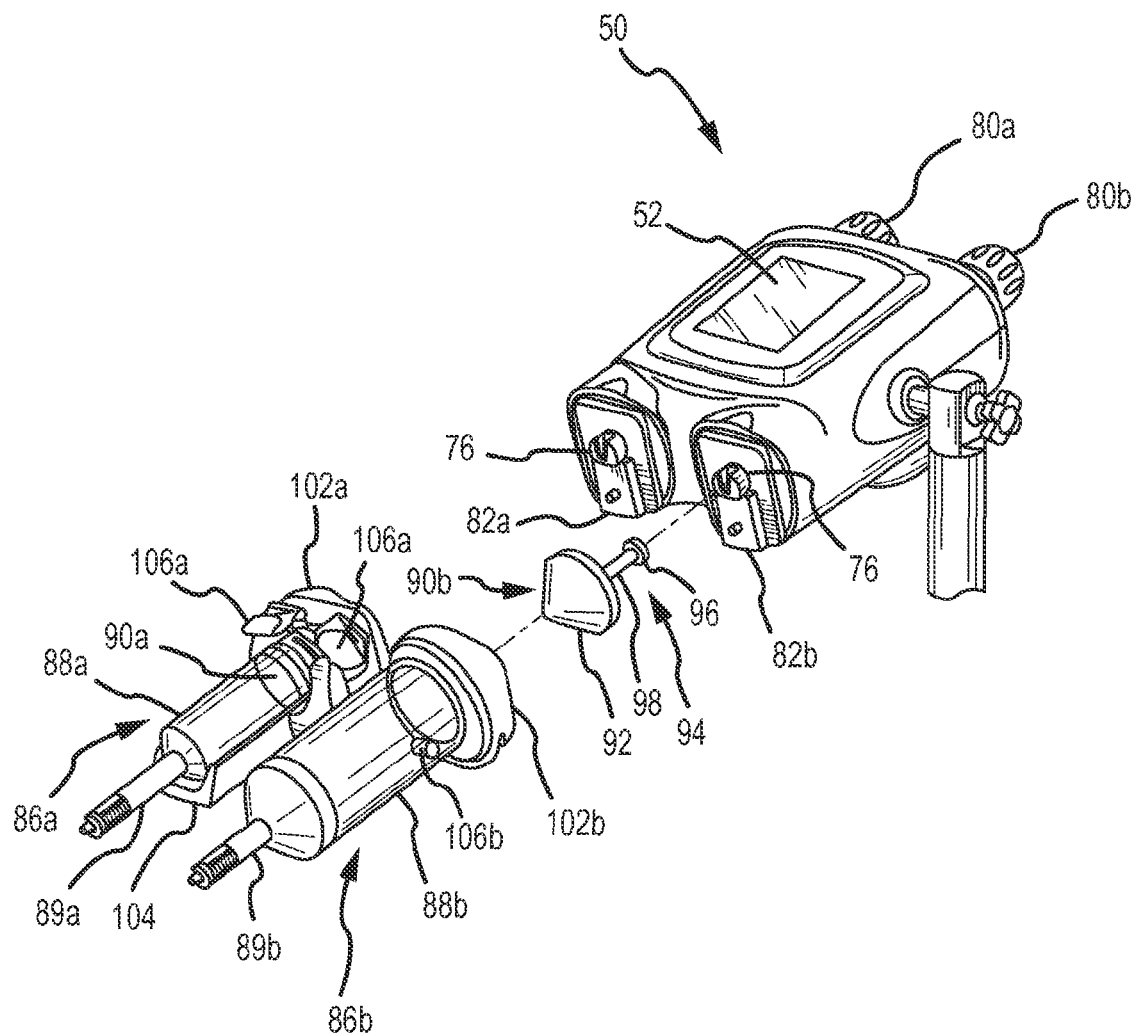
FIG. 2B is an enlarged, partially exploded, perspective view of a powerhead used by the power injector of FIG. 2A.

Various details regarding the integration of the syringes 86*a*, 86*b* with the powerhead 50 are presented in FIG. 2B. Each of the syringes 86*a*, 86*b* includes the same general components. The syringe 86*a* includes plunger or piston 90*a* that is movably disposed within a syringe barrel 88*a*. Movement of the plunger 90*a* along an axis 100*a* (FIG. 2A) via operation of the powerhead 50 will discharge fluid from within the syringe barrel 88*a* through a nozzle 89*a* of the syringe 86*a*. An appropriate conduit (not shown) will typically be fluidly interconnected with the nozzle 89*a* in any appropriate manner to direct fluid to a desired location (e.g., a patient). Similarly, the syringe 86*b* includes plunger or piston 90*b* that is movably disposed within a syringe barrel 88*b*. Movement of the plunger 90*b* along an axis 100*b* (FIG. 2A) via operation of the powerhead 50 will discharge fluid from within the syringe barrel 88*b* through a nozzle 89*b* of the syringe 86*b*. An appropriate conduit (not shown) will typically be fluidly interconnected with the nozzle 89*b* in any appropriate manner to direct fluid to a desired location (e.g., a patient).

The syringe 86*a* is interconnected with the powerhead 50 via an intermediate faceplate 102*a*. This faceplate 102*a* includes a cradle 104 that supports at least part of the syringe barrel 88*a*, and which may provide/accommodate any additional functionality or combination of functionalities. A mounting 82*a* is disposed on and is fixed relative to the powerhead 50 for interfacing with the faceplate 102*a*. A ram coupler 76 of a ram 74, which are each part of a syringe plunger drive assembly 56 for the syringe 86*a*, is positioned in proximity to the faceplate 102*a* when mounted on the powerhead 50. Details regarding the syringe plunger drive assembly 56 will be discussed in more detail below in relation to FIG. 2C. Generally, the ram coupler 76 may be coupled with the syringe plunger 90*a* of the syringe 86*a*, and the ram coupler 76 and ram 74 may then be moved relative to the powerhead 50 to move the syringe plunger 90*a* along the axis 100*a* (FIG. 2A). It may be such that the ram coupler 76 is engaged with, but not actually coupled to, the syringe plunger 90*a* when moving the syringe plunger 90*a* to discharge fluid through the nozzle 89*a* of the syringe 66*a*.

The faceplate 102*a* may be moved at least generally within a plane that is orthogonal to the axes 100*a*, 100*b* (associated with movement of the syringe plungers 90*a*, 90*b*, respectively, and illustrated in FIG. 2A), both to mount the faceplate 102*a* on and remove the faceplate 102*a* from its mounting 82*a* on the powerhead 50. The faceplate 102*a* may be used to couple the syringe plunger 90*a* with its corresponding ram coupler 76 on the powerhead 50. In this regard, the faceplate 102*a* includes a pair of bandies 106*a*. Generally and with the syringe 86*a* being initially positioned within the faceplate 102*a*, the handles 106*a* may be moved to in turn move/translate the syringe 86*a* at least generally within a plane that is orthogonal to the axes 100*a*, 100*b* (associated with movement of the syringe plungers 90*a*, 90*b*, respectively, and illustrated in FIG. 2A). Moving the handles 106*a* to one position moves/translates the syringe 86*a* (relative to the faceplate 102*a*) in an at least generally downward direction to couple its syringe plunger 90*a* with its corresponding ram coupler 76. Moving the handles 106*a* to another position moves/translates the syringe 86*a* (relative to the faceplate 102*a*) in an at least generally upward direction to uncouple its syringe plunger 90*a* from its corresponding ram coupler 76.

The syringe 86*b* is interconnected with the powerhead 50 via an intermediate faceplate 102*b*. A mounting 82*b* is disposed on and is fixed relative to the powerhead 50 for interfacing with the faceplate 102*b*. A ram coupler 76 of a ram 74, which are each part of a syringe plunger drive assembly or syringe plunger driver 56 for the syringe 86*b*, is positioned in proximity to the faceplate 102*b* when mounted to the powerhead 50. Details regarding the syringe plunger drive assembly 56 again will be discussed in more detail below in relation to FIG. 2C. Generally, the ram coupler 76 may be coupled with the syringe plunger 90*b* of the syringe 86*b*, and the ram coupler 76 and ram 74 may be moved relative to the powerhead 50 to move the syringe plunger 90*b* along the axis 100*b*

(FIG. 2A). It may be such that the ram coupler 76 is engaged with, but not actually coupled to, the syringe plunger 90b when moving the syringe plunger 90b to discharge fluid through the nozzle 89b of the syringe 86b.

The faceplate 102b may be moved at least generally within a plane that is orthogonal to the axes 100a, 100b (associated with movement of the syringe plungers 90a, 90b, respectively, and illustrated in FIG. 2A), both to mount the faceplate 102b on and remove the faceplate 102b from its mounting 82b on the powerhead 50. The faceplate 102b also may be used to couple the syringe plunger 90b with its corresponding ram coupler 76 on the powerhead 50. In this regard, the faceplate 102b may include a handle 106b. Generally and with the syringe 86b being initially positioned within the faceplate 102b, the syringe 86b may be rotated along its long axis 100b (FIG. 2A) and relative to the faceplate 102b. This rotation may be realized by moving the handle 106b, by grasping and turning the syringe 86b, or both. In any case, this rotation moves/translates both the syringe 86b and the faceplate 102b at least generally within a plane that is orthogonal to the axes 100a, 100b (associated with movement of the syringe plungers 90a, 90b, respectively, and illustrated in FIG. 2A). Rotating the syringe 86b in one direction moves/translates the syringe 86b and faceplate 102b in an at least generally downward direction to couple the syringe plunger 90b with its corresponding ram coupler 76. Rotating the syringe 86b in the opposite direction moves/translates the syringe 86b and faceplate 102b in an at least generally upward direction to uncouple its syringe plunger 90b from its corresponding ram coupler 76.

As illustrated in FIG. 2B, the syringe plunger 90b includes a plunger body 92 and a syringe plunger coupler 94. This syringe plunger coupler 94 includes a shaft 98 that extends from the plunger body 92, along with a head 96 that is spaced from the plunger body 92. Each of the ram couplers 76 includes a larger slot that is positioned behind a smaller slot on the face of the ram coupler 76. The head 96 of the syringe plunger coupler 94 may be positioned within the larger slot of the ram coupler 76, and the shaft 98 of the syringe plunger coupler 94 may extend through the smaller slot on the face of the ram coupler 76 when the syringe plunger 90b and its corresponding ram coupler 76 are in a coupled state or condition. The syringe plunger 90a may include a similar syringe plunger coupler 94 for interfacing with its corresponding ram coupler 76.

Figure 2C:
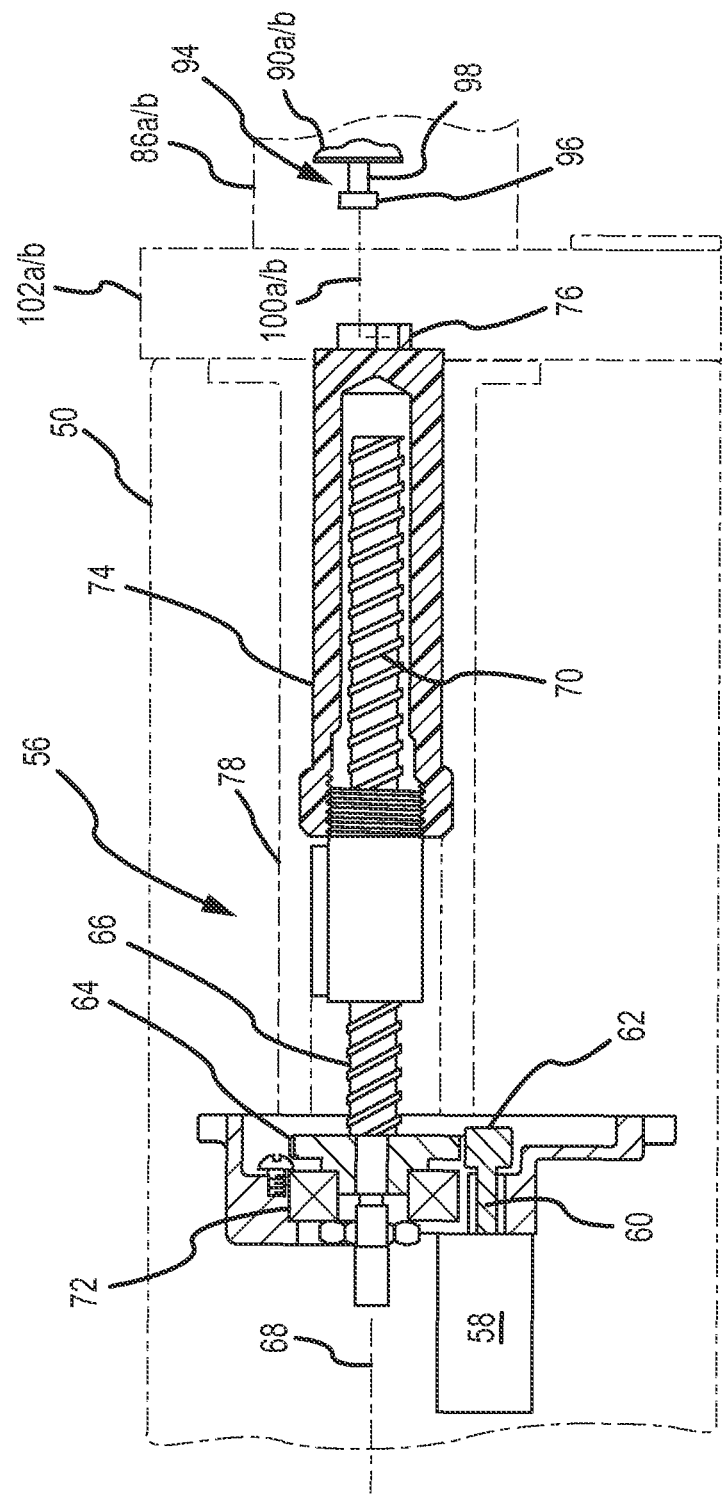
FIG. 2C is a schematic of one embodiment of a syringe plunger driver or syringe plunger drive assembly used by the power injector of FIG. 2A.

The powerhead 50 is utilized to discharge fluid from the syringes 86a, 86b in the case of the power injector 40. That is, the powerhead 50 provides the motive force to discharge fluid from each of the syringes 86a, 86b. One embodiment of what may be characterized as a syringe plunger drive assembly or syringe plunger driver is illustrated in FIG. 2C, is identified by reference numeral 56, and may be utilized by the powerhead 50 to discharge fluid from each of the syringes 86a, 86b. A separate syringe plunger drive assembly 56 may be incorporated into the powerhead 50 for each of the syringes 86a, 86b. In this regard and referring back to FIGS. 2A-B, the powerhead 50 may include hand-operated knobs 80a and 80b for use in separately controlling each of the syringe plunger drive assemblies 56.

Initially and in relation to the syringe plunger drive assembly 56 of FIG. 2C, each of its individual components may be of any appropriate size, shape, configuration and/or type. The syringe plunger drive assembly 56 includes a motor 58, which has an output shaft 60. A drive gear 62 is mounted on and rotates with the output shaft 60 of the motor 58. The drive gear 62 is engaged or is at least engageable with a driven gear 64. This driven gear 64 is mounted on and rotates with a drive screw or shaft 66. The axis about which the drive screw 66 rotates is identified by reference numeral 68. One or more bearings 72 appropriately support the drive screw 66.

A carriage or ram 74 is movably mounted on the drive screw 66. Generally, rotation of the drive screw 66 in one direction axially advances the ram 74 along the drive screw 66 (and thereby along axis 68) in the direction of the corresponding syringe 86a/b, while rotation of the drive screw 66 in the opposite direction axially advances the ram 74 along the drive screw 66 (and thereby along axis 68) away from the corresponding syringe 86a/b. In this regard, the perimeter of at least part of the drive screw 66 includes helical threads 70 that interface with at least part of the ram 74. The ram 74 is also movably mounted within an appropriate bushing 78 that does not allow the ram 74 to rotate during a rotation of the drive screw 66. Therefore, the rotation of the drive screw 66 provides for an axial movement of the ram 74 in a direction determined by the rotational direction of the drive screw 66.

The ram 74 includes a coupler 76 that that may be detachably coupled with a syringe plunger coupler 94 of the syringe plunger 90a/b of the corresponding syringe 86a/b. When the ram coupler 76 and syringe plunger coupler 94 are appropriately coupled, the syringe plunger 90a/b moves along with ram 74. FIG. 2C illustrates a configuration where the syringe 86a/b may be moved along its corresponding axis 100a/b without being coupled to the ram 74. When the syringe 86a/b is moved along its corresponding axis 100a/b such that the head 96 of its syringe plunger 90a/b is aligned with the ram coupler 76, but with the axes 68 still in the offset configuration of FIG. 2C, the syringe 86a/b may be translated within a plane that is orthogonal to the axis 68 along which the ram 74 moves. This establishes a coupled engagement between the ram coupler 76 and the syringe plunger coupler 96 in the above-noted manner.

The power injectors 10, 40 of FIGS. 1 and 2A-C each may be used for any appropriate application, including without limitation for medical imaging applications where fluid is injected into a subject (e.g., a patient). Representative medical imaging applications for the power injectors 10, 40 include without limitation computed tomography or CT imaging, magnetic resonance imaging or MRI, SPECT imaging, PET imaging, X-ray imaging, angiographic imaging, optical imaging, and ultrasound imaging. The power injectors 10, 40 each could be used alone or in combination with one or more other components. The power injectors 10, 40 each may be operatively interconnected with one or more components, for instance so that information may be conveyed between the power injector 10, 40 and one or more other components (e.g., scan delay information, injection start signal, injection rate).

Any number of syringes may be utilized by each of the power injectors 10, 40, including without limitation single-head configurations (for a single syringe) and dual-head configurations (for two syringes). In the case of a multiple syringe configuration, each power injector 10, 40 may discharge fluid from the various syringes in any appropriate manner and according to any timing sequence (e.g., sequential discharges from two or more syringes, simultaneous discharges from two or more syringes, or any combination thereof). Each such syringe utilized by each of the power injectors 10, 40 may include any appropriate fluid, for instance contrast media, a radiopharmaceutical, saline, and any combination thereof. Each such syringe utilized by each of the power injectors 10, 40 may be installed in any appropriate manner (e.g., rear-loading configurations may be utilized; front-loading configurations may be utilized; side-loading configurations may be utilized).

Figure 3:
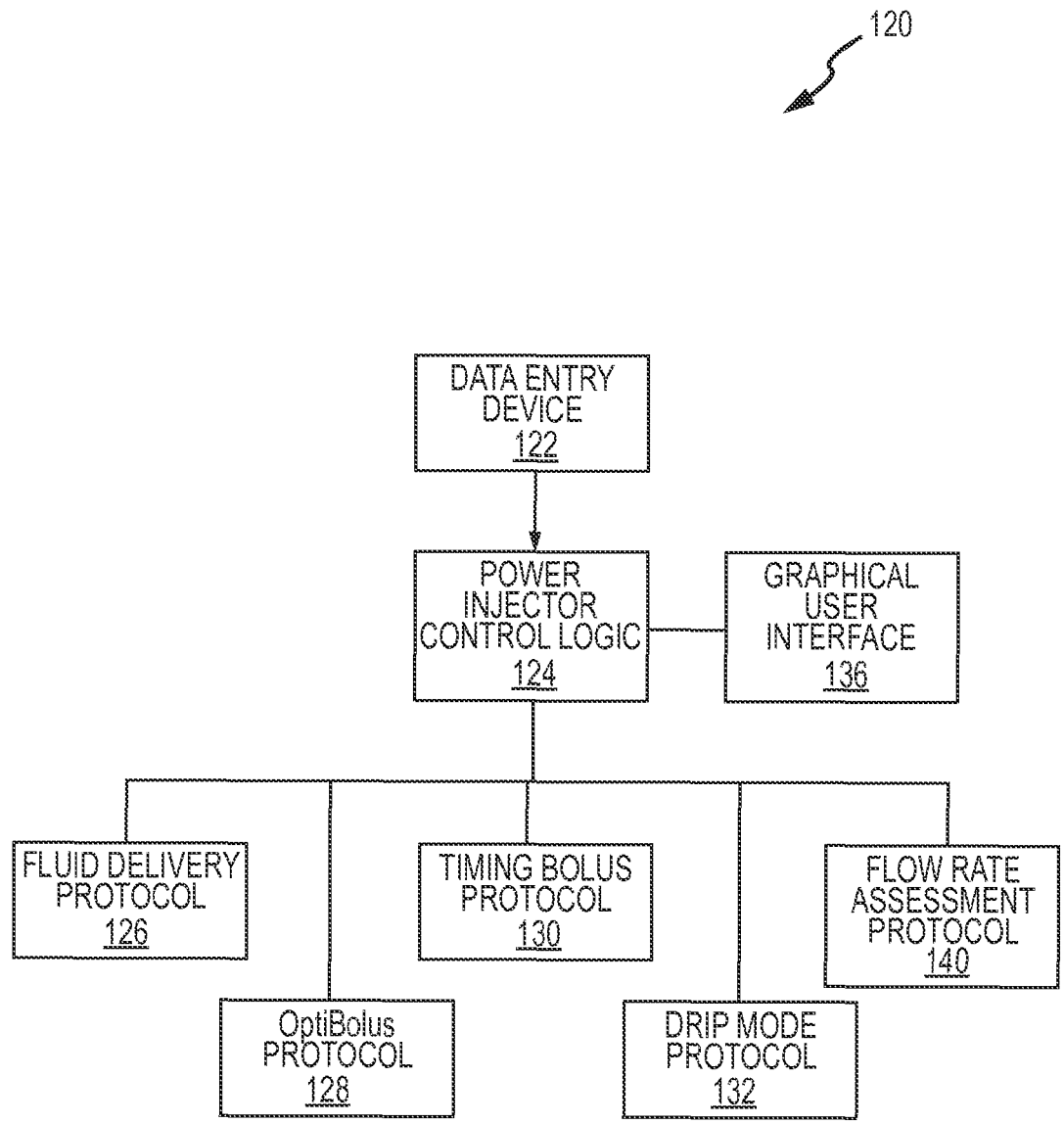
FIG. 3 is a schematic of one embodiment of a power injector control logic that may be used by the power injectors of FIGS. 1 and 2A-C.

FIG. 3 illustrates one embodiment of a power injector control system 120 that may be utilized by any appropriate power injector, including without limitation the power injector 10 of FIG. 1 and the power injector 40 of FIGS. 2A-C. The power injector control system 120 may include one or more data entry devices 122 of any appropriate configuration and/or type (e.g., a keyboard, a mouse, a touch pad, a track ball, a touch screen display, a soft key display). One or more of these data entry devices 122 may be operatively interconnected with a power control injector module or power injector control logic 124. The power injector control logic 124 may be of any appropriate form and/or configuration, may be implemented or integrated in any appropriate manner, or both (e.g., for instance in the power injector software; implemented by software, hardware, firmware, and any combination thereof). In one embodiment, the functionality of the control logic 124 is provided by one or more processors of any appropriate size, shape, configuration, and/or type. In one embodiment, the functionality of the control logic 124 is provided by one or more computers of any appropriate size, shape, configuration, and/or type. At least one graphical user interface 136 may be operatively interconnected with the power injector control logic 124 to present an appropriate output (e.g., to an operator of the corresponding power injector).

The power injector control logic 124 may be configured to include at least one fluid delivery or injection protocol 126 (e.g., for a medical application, and which may be referred to as a medical fluid delivery procedure or operation) and a flow rate assessment protocol 140, and each of which may be in the form of a programmed sequence. For a medical fluid application, the protocol 126 thereby may be referred to as a medical fluid delivery protocol 126. Each fluid delivery protocol 126 may be configured to control the manner in which one or more fluids are being delivered to a fluid target, such as by being injected into a patient. A particular fluid delivery protocol 126 may be configured to deliver a programmed volume of a first fluid at a programmed flow rate, as well as a programmed volume of a second fluid at a programmed flow rate. Each delivery of each of the first and second fluids may be characterized as a phase. One or more phases may be utilized for each of the first and second fluids. In one embodiment, the first fluid is contrast media and the second fluid is saline. The flow rate assessment protocol 140 will be discussed in more detail below, but generally is configured to provide comparative flow rate information during execution of a fluid delivery protocol 126.

The power injector control logic 124 of FIG. 3 may include one or more additional protocols as desired/required, and each of which may be in the form of a programmed sequence. Representative protocols that may be utilized by the power injector control logic 124 as desired/required, in addition to at least one fluid delivery protocol 126 and a flow rate assessment protocol 140, include without limitation an OptiBolus® protocol 128, a Timing Bolus® protocol 130, and a drip mode protocol 132. Generally, the OptiBolus® protocol 128 may be configured to deliver an exponentially decaying flow rate injection that optimizes the contrast usage and provides an extended period of uniform enhancement of the area of interest. The Timing Bolus® injection protocol 130 may be configured to provide a timing bolus injection—a small volume of contrast media, followed by a small volume of saline—to a patient for purposes of determining the optimal scan delay needed to capture the contrast media in the area of interest. The drip mode protocol 132 may be configured to provide a drip injection—a low flow rate injection of a small volume of saline delivered to the patient to keep open the fluid pathway from the power injector to the patient.

Figure 4:
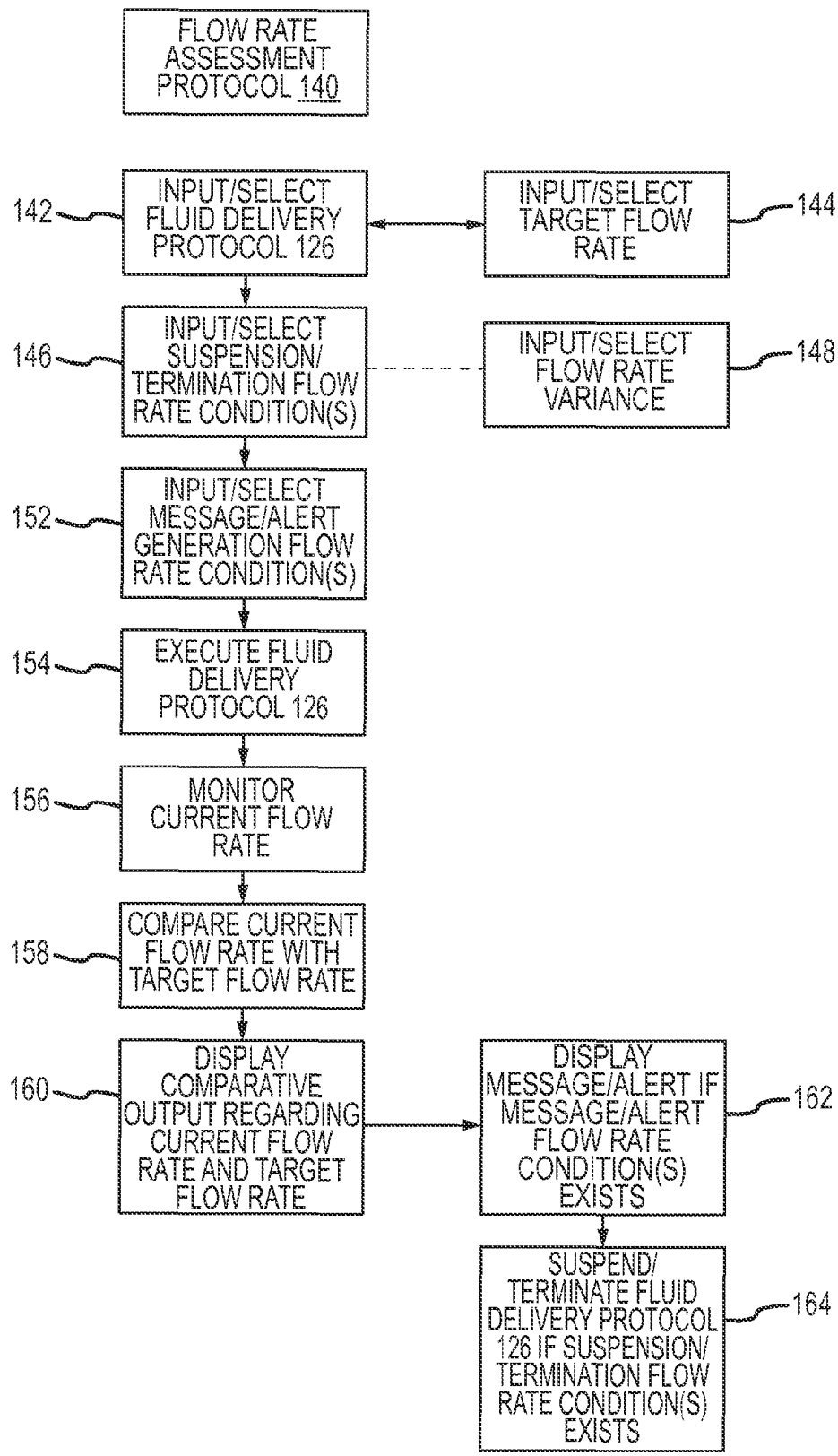
FIG. 4 is a schematic of one embodiment of a flow rate assessment protocol that may be used by the power injector control logic of FIG. 3.

One embodiment of a flow rate assessment protocol is illustrated in FIG. 4, is identified by reference numeral 140, and may be utilized by the power injector control logic 124 of FIG. 3. In one embodiment, the flow rate assessment protocol 140 is implemented by software, hardware, firmware, and any combination thereof. In one embodiment, the functionality of the flow rate assessment protocol 140 is implemented using one or more processors of any appropriate size, shape, configuration, and/or type. In one embodiment, the functionality of the flow rate assessment protocol 140 is implemented using one or more computers of any appropriate size, shape, configuration, and/or type.

A number of parameters or the like may be input or selected in any appropriate manner, and in any appropriate order in relation to the flow rate assessment protocol 140. A fluid delivery protocol 126 may be input or selected through execution of step 142. For instance, the data entry device 122 of FIG. 3 may be used to input/edit one or more parameters that will at least partially define a fluid delivery protocol 126, to retrieve a stored fluid delivery protocol 126 from memory, or both. One of these parameters may be in the form of at least one programmed or target flow rate (step 144). Multiple phases may define a fluid delivery protocol 126, and each of these phases may have its own corresponding programmed/target flow rate.

Another parameter for purposes of the flow rate assessment protocol 140 of FIG. 4 is a suspension/termination flow rate condition (step 146). One or more suspension/termination flow rate conditions may be input or selected in any appropriate manner through execution of step 146. A suspension/termination flow rate condition is generally a condition which, if encountered during execution of a fluid delivery protocol 126, will result in or trigger a suspension or termination of the fluid delivery protocol 126. Any appropriate flow rate condition may result in or trigger a suspension or termination of the fluid delivery protocol 126 for purposes of the flow rate assessment protocol 140.

In one embodiment and referring to step 148 of the flow rate assessment protocol 140 of FIG. 4, a suspension/termination flow rate condition is in the form of a flow rate variance. This flow rate variance may be in any appropriate form and determined/expressed in any appropriate manner, but is generally indicative that there is some unacceptable difference between the target flow rate (step 144) and a current or actual flow rate (step 156) that may exist during execution of the fluid delivery protocol 126. In one embodiment, the flow rate variance is limited to the actual flow rate not exceeding the target flow rate, although this may not be required in all instances. Multiple phases again may define a fluid delivery protocol 126, and each of these phases may have its own corresponding suspension/termination flow rate condition (step 146).

The flow rate assessment protocol 140 of FIG. 4 also accommodates inputting/selecting at least one message/alert generation flow rate condition or flow rate variance in any appropriate manner (step 152). A message/alert generation flow rate condition is generally a condition which, if encountered during execution of a fluid delivery protocol 126, will result in or trigger issuance of at least one message or alert. Any appropriate message, alert, or combination thereof may be utilized for purposes of step 152. Any appropriate flow rate condition may result in or trigger of at least one message or alert. The flow rate condition for purposes of step 152 may be of the same or a different type as the flow rate condition associated with step 146, may be of the same or a different magnitude as the flow rate condition associated with step 146, or both. Multiple phases again may define a fluid delivery protocol 126, and each of these phases may have its own corresponding message/alert flow rate condition (step 152).

Steps 142, 146, and 152 of the flow rate assessment protocol 140 of FIG. 4 may be executed in any appropriate manner and in any appropriate order. Although each of steps 146 and 152 may be utilized by the flow rate assessment protocol 140, one or both of these steps may not be required in all instances.

Once the flow rate assessment protocol 140 of FIG. 4 has been configured as desired/required, a fluid delivery protocol 126 may be executed in accordance with step 154. An actual or current flow rate is monitored through execution of step 156 and during the execution of the fluid delivery protocol 126 (step 154). This actual or current flow rate is that which is being realized or produced at any given point in time. The flow rate may be monitored in any appropriate manner, and flow rate information acquired by step 156 may be updated on any appropriate basis.

The actual or current flow rate (step 156) is compared with the programmed or target flow rate (step 144) pursuant to step 158 of the flow rate assessment protocol 140 of FIG. 4. The comparison of the actual/current flow rate with the programmed/target flow rate may be undertaken in any appropriate manner for purposes of step 158, and this comparison may be initiated/updated on any appropriate basis. Step 160 is directed to displaying a comparative output regarding the actual/current flow rate (step 156) and the programmed/target flow rate (144). This comparative output may be displayed at any appropriate location or combination of locations (e.g., on a graphical user interface associated with the power injector), may be displayed on any appropriate basis, or both. In one embodiment, the comparative output from step 160 is continuously displayed. In another embodiment, the comparative output from step 160 is displayed only when a certain relationship develops or exists between the actual/current flow rate and the programmed/target flow rate (e.g., when at least a certain differential or flow rate variance exists between the actual/current flow rate and the programmed/target flow rate).

Steps 162 and 164 of the flow rate assessment protocol 140 relate to steps 152 and 146, respectively. Step 162 is directed to displaying at least one message, at least one alert, or both, if at least one flow rate condition or flow rate variance exists. Step 164 is directed to suspending or terminating the execution of the fluid delivery protocol 126 (or more generally making at least one change in relation to the fluid delivery protocol 126) if at least one suspension/termination flow rate condition or flow rate variance exists. Once again, although the same flow rate condition or flow rate variance may trigger the execution of each of steps 162 and 164, such need not always be the case. For instance, at least one message or alert may be issued through execution of step 162 if a first flow rate condition or first flow rate variance exists, while the fluid delivery protocol 126 may be suspended or terminated through execution of step 164 if a different, second flow rate condition or second flow rate variance exists.

Figure 5:
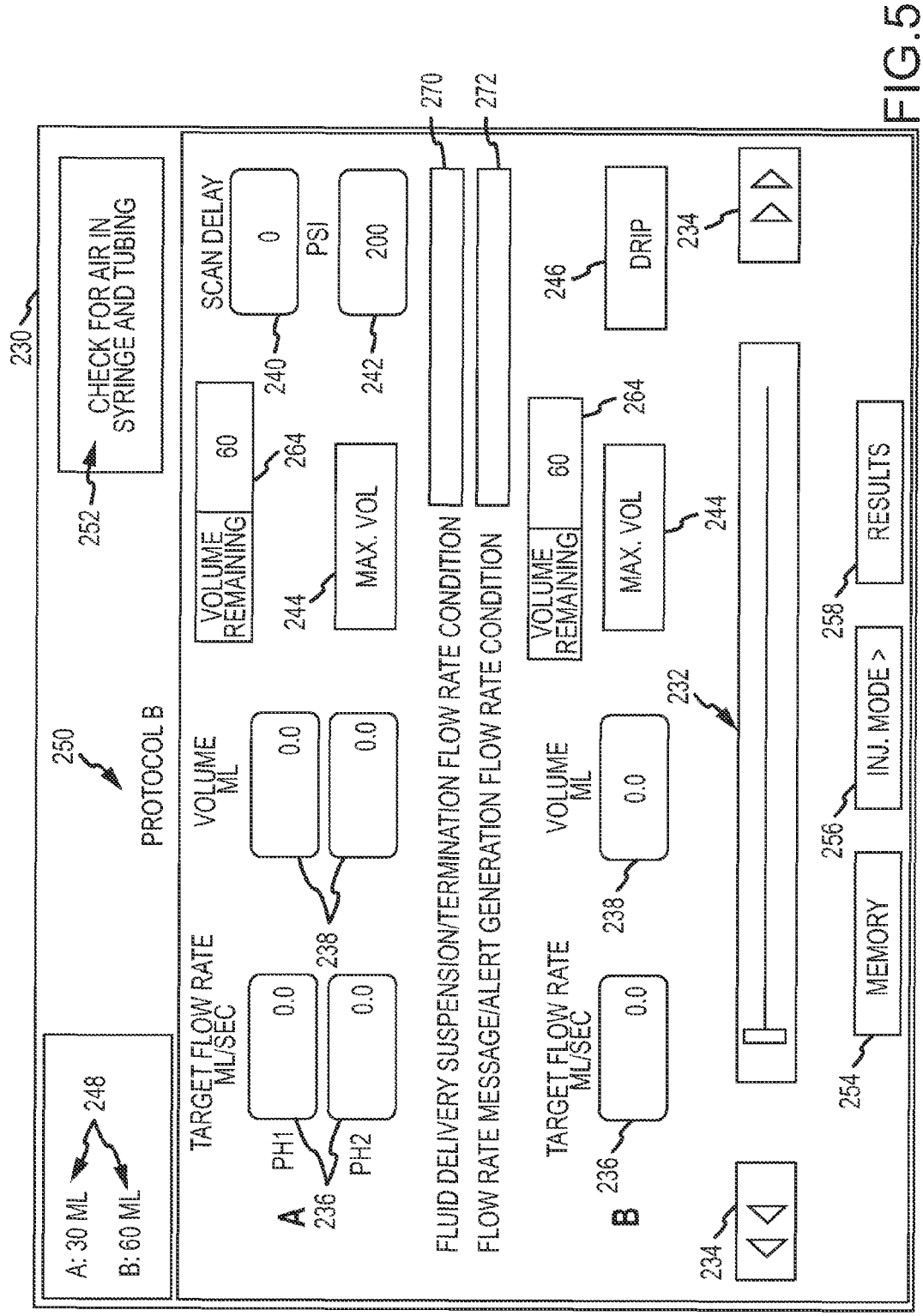
FIG. 5 is one embodiment of a setup screen for a power injector graphical user interface, and that may incorporate/embody one or more aspects of the flow rate assessment protocol of FIG. 4.

One embodiment of a setup screen is illustrated in FIG. 5 and is identified by reference numeral 230. Although the setup screen 230 may be adapted for use with any power injector configuration, it will be described herein in relation to the power injector 10 of FIG. 1. This setup screen 230 may be presented on the graphical user interface 11 for the power injector 10 of FIG. 1, and is configured to execute various steps or implement various aspects of the flow rate assessment protocol 140 of FIG. 4. The setup screen 230 is for the case of the power injector 10 of FIG. 1 being of a dual-head configuration—utilizing a pair of syringes 28 (one defining an A side of the power injector 10, and another defining a B side of the power injector 10). Each of the A and B sides may contain any appropriate fluid (e.g., contrast media, a radiopharmaceutical, saline, and any combination thereof). In addition, the setup screen 230 is configured for providing two phases on the A side of the power injector 10, and a single phase on the B side of the power injector 10. Any number of phases may be utilized by each of the A and B sides of the power injector 10, and the setup screen 230 may be configured accordingly. The power injector control logic 124 of FIG. 3 may be configured to store multiple setup screens 230, each of which may use a different combination of phases for the A and B sides of the power injector 10.

The setup screen 230 from FIG. 5 may include various buttons to access various other system screens on the power injector graphical user interface 11, including a memory button 254 (e.g., for accessing an injection or fluid delivery protocol 126 that is stored), an injection mode button 256 (e.g., for initiating an injection procedure or fluid delivery protocol 126), and a results button 258 (e.g., for displaying results on an injection procedure or fluid delivery protocol 126). The setup screen 230 also accommodates displaying, entering, and/or editing various parameters that relate to the fluid delivery protocol 126. For instance, the suspension/termination flow rate condition or flow rate variance associated with steps 146 and 164 of the flow rate assessment protocol 140 may be displayed, entered, and/or edited in a segment 270. The flow rate message/alert generation flow rate condition or flow rate variance associated with steps 152 and 162 of the flow rate assessment protocol 140 may be displayed, entered, and/or edited in a segment 272.

The setup screen 230 of FIG. 5 may also include the following: 1) a slide bar 232 for displaying/changing a value for a selected parameter presented on the setup screen 230; 2) adjustment arrows 234 for providing a more refined adjustment of a value for a selected parameter presented on the setup screen 230; 3) a pair of programmed/target flow rate segments 236 to accommodate displaying, entering, and/or editing the desired rate of delivery of contrast media or other fluid from the A side of the power injector 10 (one for each of two phases), and another programmed/target flow rate segment 236 to accommodate displaying, entering, and/or editing the desired rate of delivery of saline or other fluid from the B side of the power injector 10 (e.g., for step 144 of the flow rate assessment protocol 140 of FIG. 4); 4) an injection volume segment 238 to accommodate displaying, entering, and/or editing the desired volume to be injected from the syringe 28 for each of the A and B sides of the power injector 10; 5) a remaining volume indicator 264 to depict the projected volume remaining in the syringe 28 for each of the A and B sides of the power injector 10; 6) a scan delay indicator 240 to depict the time counted down from the start of an injection or fluid delivery so that an operator may accurately delay a scanner being used in combination with the power injector 10; 7) a pressure limit segment 242 for the syringe 28 on the A side of the power injector 10; 8) a maximum volume indicator 244 for each of the A and B sides of the power injector 10, which indicates the volume currently available in the associated syringe 28, and which may blink if the volume needed for an injection or fluid delivery procedure exceeds the available volume in the associated syringe 28; 9) a drip mode button or key 246 to access a drip mode functionality for the power injector 10 (e.g., a "drip injection" being a low flow rate injection of a small volume of fluid (e.g. saline) delivered to a patient in order to keep the fluid pathway to the patient in an open condition); 10) a pair of syringe size indicators 248 for each of the A and B sides of the power injector 10; 11) a protocol identifier 250 (e.g., to identify the injection or fluid delivery protocol being used to operate the power injector 10); and 12) a message 252 (e.g., for an operator).

Any data entry device may be utilized to enter the desired/required information on the setup screen 230 of FIG. 5, such as a keyboard, mouse, and/or by presenting the setup screen 230 on a touch screen display. The various inputs on the setup screen 230 configure both the fluid delivery protocol 126 and the flow rate assessment protocol 140 of the power injector control logic 124 (FIG. 3). Various options for presenting comparative output (step 160 of the flow rate assessment protocol 140 of FIG. 4) will now be addressed in relation to FIGS. 6A-D.

Various embodiments of progress screens are illustrated in FIGS. 6A-D, and are representative of screens that may be presented on a power injector graphical user interface 11 during execution of a fluid delivery protocol 126. Each of these progress screens are for the case of the power injector 10 of FIG. 1 being of a dual-head configuration—utilizing a pair of syringes 28 (one defining an A side of the power injector 10, and another defining a B side of the power injector 10). In addition, the various progress screens are each configured for providing two phases on the A side of the power injector 10, and a single phase on the B side of the power injector 10. Any number of phases may be utilized by each of the A and B sides of the power injector 10, and the various progress screens may be configured accordingly.

The progress screens of FIGS. 6A-D generally display the progress of an injection procedure or the execution of a fluid delivery protocol 126 that is currently being performed by the power injector 10. Various buttons or keys that may be selected/activated in any appropriate manner may be included on these progress screens to provide any appropriate function or combination of functions, including a stop button 312 (e.g., to stop operation of the power injector 10, or more specifically the delivery of fluid from the power injector 10). These progress screens also include the following: 1) injection indicators 314 for each of the A and B sides of the power injector 10, and which may flash to indicate when fluid is being delivered from the corresponding side; 2) a remaining volume indicator 316 for each of the A and B sides of the power injector 10, and which indicates the amount of volume remaining in the associated syringe 28; 3) a programmed volume indicator 320 for each of the two phases being utilized by the fluid delivery protocol 126 on the A side of the power injector 10, and a programmed volume indicator 320 for the B side of the power injector 10, where each programmed volume indicator 320 displays the corresponding programmed volume for the fluid delivery protocol 126 currently being executed by the power injector 10; 4) an elapsed time indicator 322 that depicts the amount of time that has passed from the start of the fluid delivery protocol 126; 5) a scan delay indicator 324 to depict the time counted down from the start of an injection so that an operator may accurately delay a scanner being used in combination with the power injector 10; and 6) a pressure indicator 326 that may show the current pressure and the pre-set pressure limit value (the vertical line representing the pre-set pressure limit value, and the horizontal line representing the current pressure). Each of the progress screens of FIGS. 6A-D displays a different comparative output regarding the programmed/target flow rate (step 144) and the actual/current flow rate (step 156) for the flow rate assessment protocol 140 of FIG. 4. The different comparative outputs provided by each of these progress screens will now be addressed. Although each of these comparative outputs are separately included on a progress screen, any appropriate number of comparative outputs could be included on any progress screen.

Figure 6A:
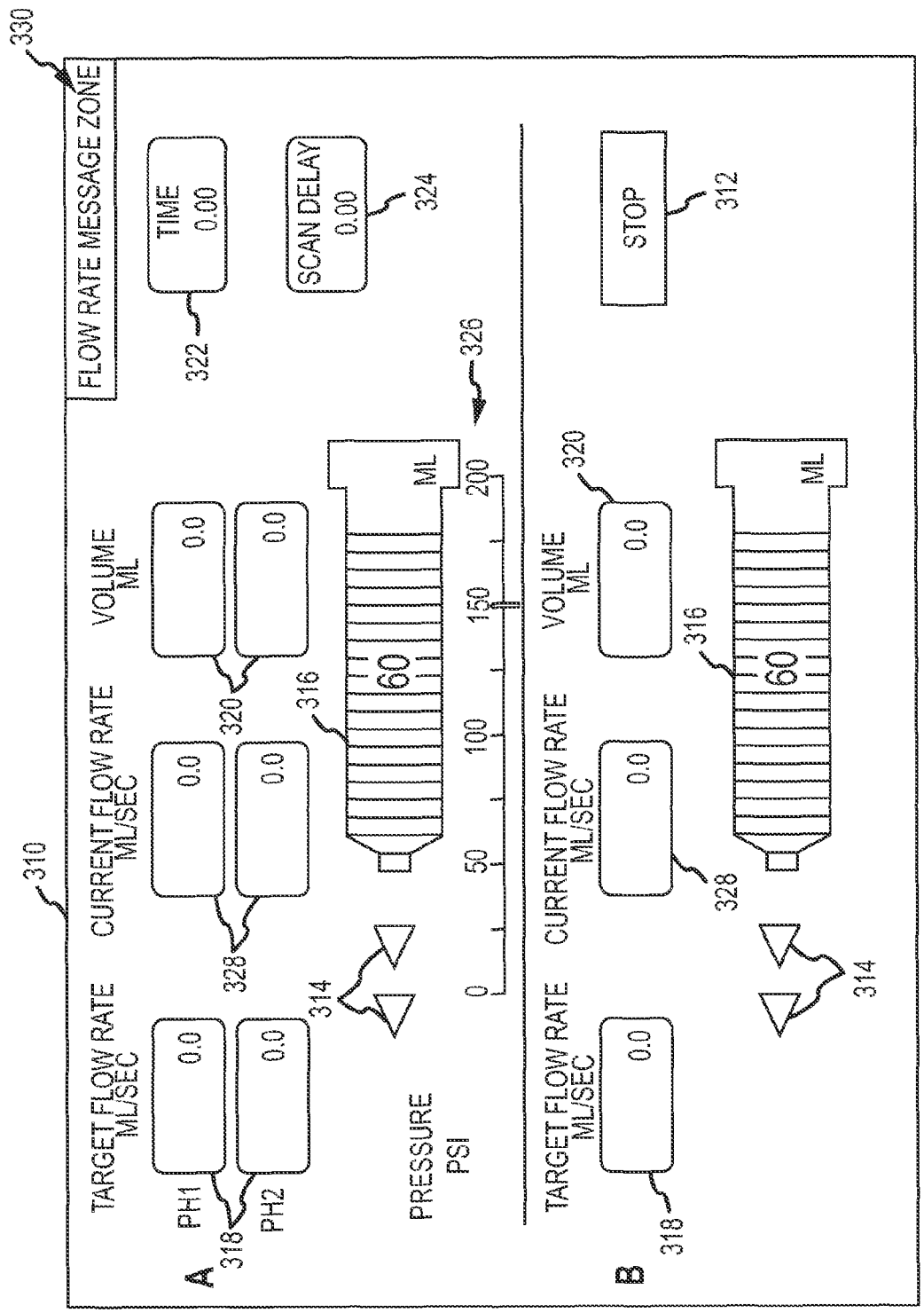
FIG. 6A is one embodiment of a progress screen for a power injector graphical user interface, which is configured to numerically display both a target flow rate and a current flow rate.

The progress screen 310 of FIG. 6A numerically displays both a programmed/target flow rate (step 144 of the flow rate assessment protocol 140 of FIG. 4) and an actual/current flow rate (step 156 of the flow rate assessment protocol 140 of FIG. 4). More specifically, the progress screen 310 includes a programmed/target flow rate indicator 318 for each of the two phases being utilized by the fluid delivery protocol 126 on the A side of the power injector 10, and a programmed/target flow rate indicator 318 for the B side of the power injector 10, where each programmed/target flow rate indicator 318 displays the corresponding programmed/target flow rate for the fluid delivery protocol 126 currently being executed by the power injector 10 (e.g., step 160 of the flow rate assessment protocol 140).

An actual/current flow rate indicator 328 is also displayed for each of the two phases being utilized by the fluid delivery protocol 126 on the A side of the power injector 10, and another actual/current flow rate indicator 328 is displayed for the B side of the power injector 10, where each actual/current flow rate indicator 328 displays the corresponding actual/current flow rate for the fluid delivery protocol 126 currently being executed by the power injector 10 (e.g., step 160 of the flow rate assessment protocol 140 of FIG. 4). Any appropriate message 330 regarding a flow rate condition or flow rate variance may be displayed on the progress screen 310 (e.g., in accordance with step 162 of the flow rate assessment protocol 140). This flow rate condition message 330 may be in any appropriate form as well (e.g., textual; graphical; textual and graphical).

Figure 6B:
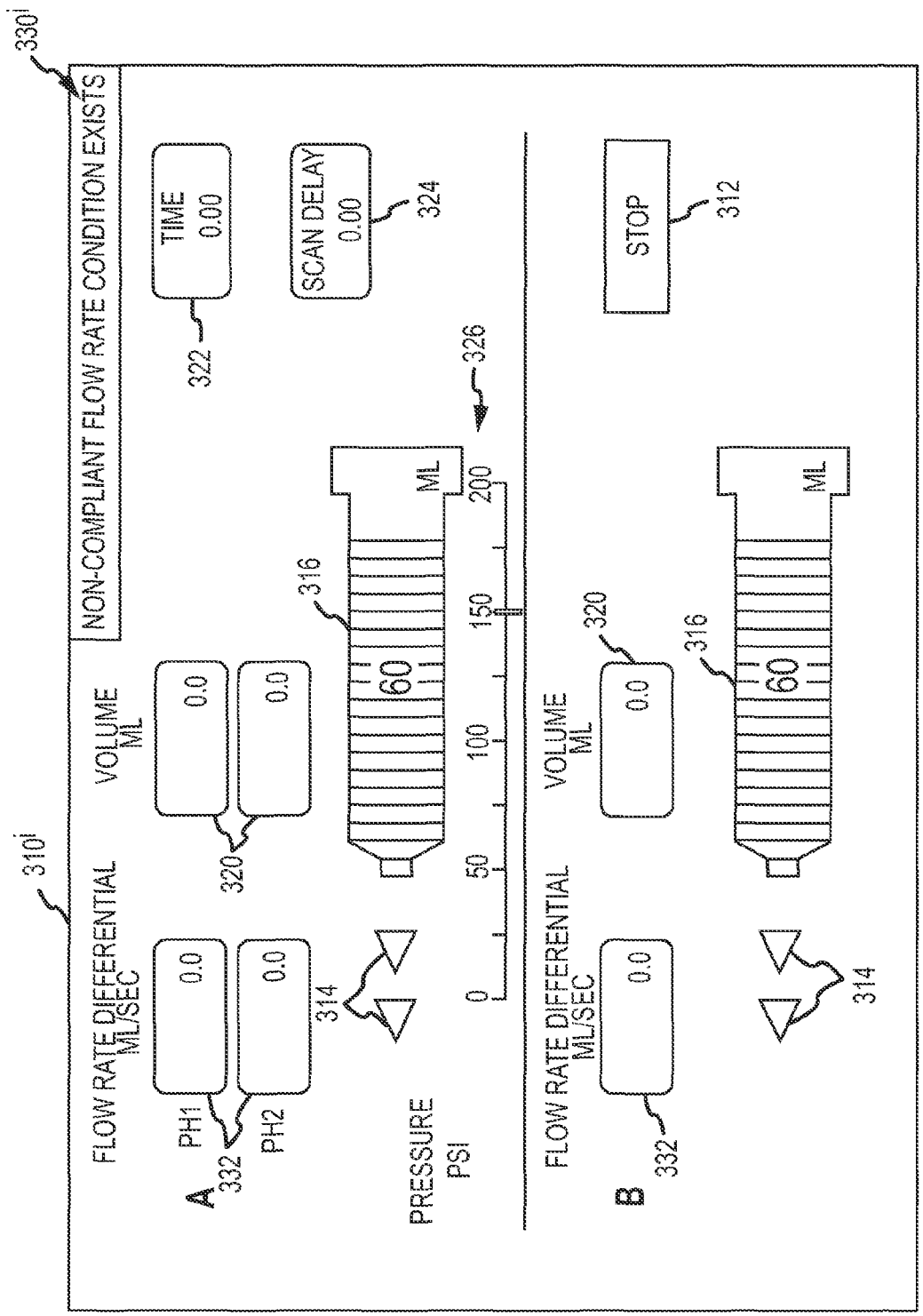
FIG. 6B is one embodiment of a progress screen for a power injector graphical user interface, which is configured to display a flow rate differential for a target flow rate and a current flow rate.

The progress screen 310$^i$ of FIG. 6B displays a differential flow rate indicator 332 for each of the two phases being utilized by the fluid delivery protocol 126 on the A side of the power injector 10, and another differential flow rate indicator 332 for the B side of the power injector 10. Each differential flow rate indicator 332 displays the difference between the corresponding programmed/target flow rate and the corresponding actual/current flow rate for the fluid delivery protocol 126 currently being executed by the power injector 10 (e.g., step 160 of the flow rate assessment protocol 140). A positive differential flow rate indicator 332 may indicate that the corresponding actual/current flow rate is greater than the corresponding programmed/target flow rate by the noted numerical value (if the actual/current flow rate is allowed to exceed the programmed/target flow rate, which may not be the case (e.g., for safety reasons)), while a negative differential flow rate indicator 332 may indicate that the corresponding actual/current flow rate is less than the corresponding programmed/target flow rate by the noted numerical value, or vice versa. A representative flow rate condition message 330$^i$ may also be displayed on the progress screen 310$^i$ (e.g., in accordance with step 162 of the flow rate assessment protocol 140 of FIG. 4).

Figure 6C:
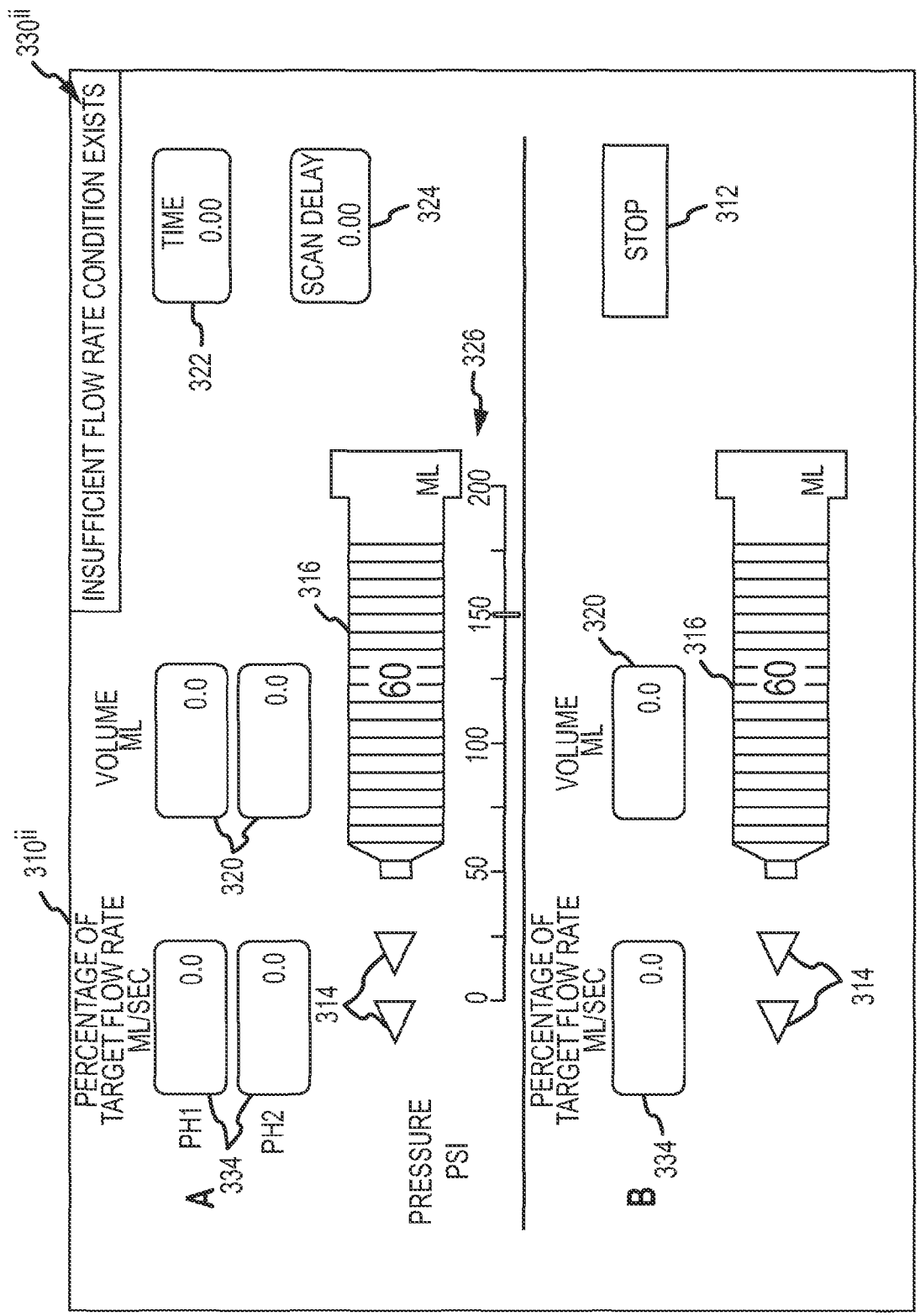
FIG. 6C is one embodiment of a progress screen for a power injector graphical user interface, which is configured to display a current flow rate as a percentage of a target flow rate.

The progress screen 310$^{ii}$ of FIG. 6C displays a percentage flow rate indicator 334 for each of the two phases being utilized by the fluid delivery protocol 126 on the A side of the power injector 10, and another percentage flow rate indicator 334 for the B side of the power injector 10. Each percentage flow rate indicator 334 displays the actual/current flow rate as a percentage of the corresponding programmed/target flow rate for the fluid delivery protocol 126 currently being executed by the power injector 10 (e.g., step 160 of the flow rate assessment protocol 140). A percentage flow rate indicator 334 in excess of 100 may indicate that the corresponding actual/current flow rate is greater than the corresponding programmed/target flow rate by the difference between noted numerical value and 100 (if the actual/current flow rate is allowed to exceed the programmed/target flow rate, which may not be the case (e.g., for safety reasons)), while a percentage flow rate indicator 334 less than 100 may indicate that the corresponding actual/current flow rate is less than the corresponding programmed/target flow rate by the difference between the noted numerical value and 100. A representative flow rate condition message 330$^{ii}$ may also be displayed on the progress screen 310$^{ii}$ (e.g., in accordance with step 162 of the flow rate assessment protocol 140 of FIG. 4).

Figure 6D:
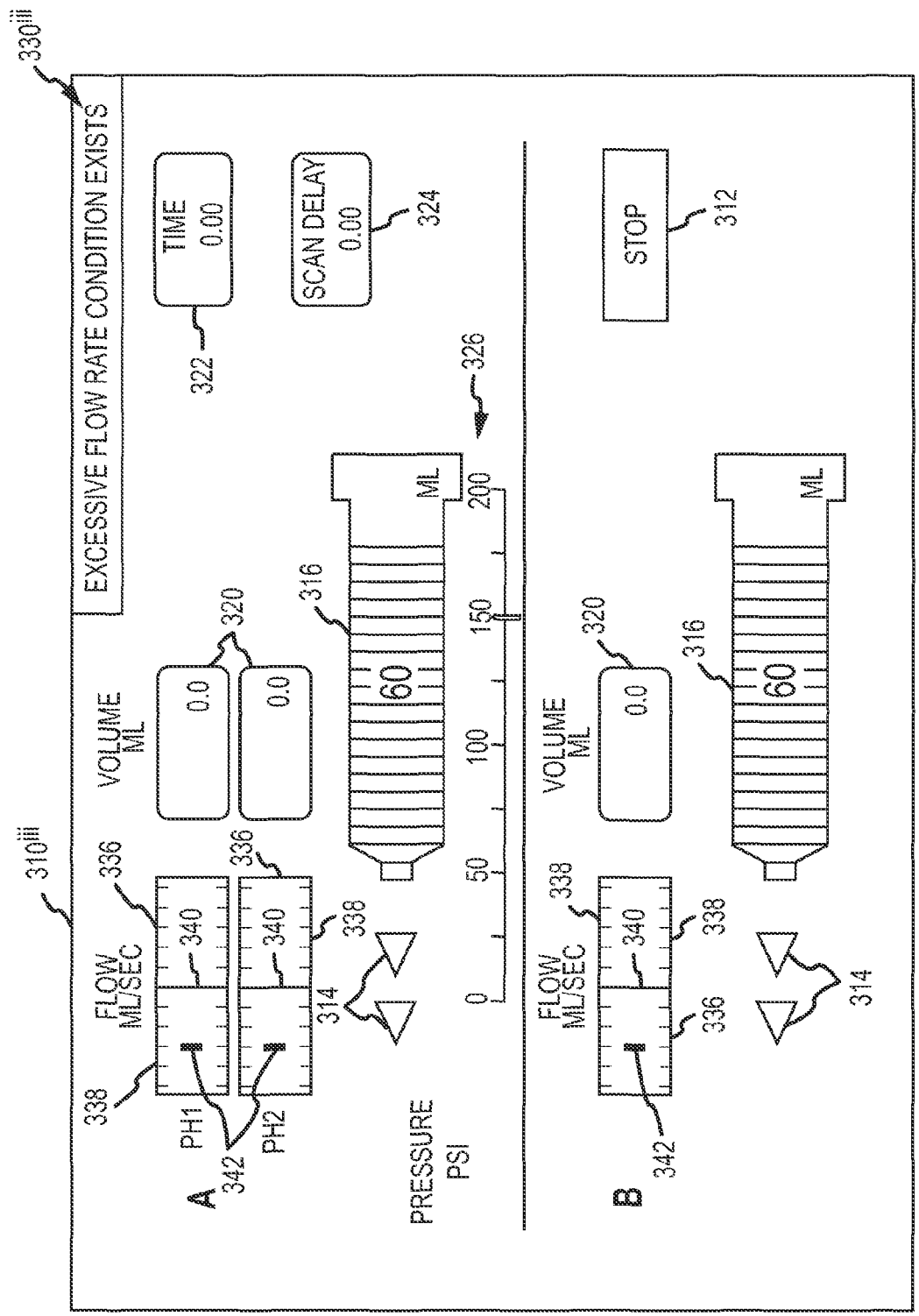
FIG. 6D is one embodiment of a progress screen for a power injector graphical user interface, which is configured to graphically display both a target flow rate and a current flow rate.

The progress screen 310$^{iii}$ of FIG. 6D graphically displays both a programmed/target flow rate and an actual/current flow rate. More specifically, the progress screen 310$^{iii}$ includes a flow rate meter 336 for each of the two phases being utilized by the fluid delivery protocol 126 on the A side of the power injector 10, and another flow rate meter 336 for the B side of the power injector 10. Each flow rate meter 336 includes a plurality of gradations 338, along with a programmed/target flow rate indicator 340 and an actual/current flow rate indicator 342. The programmed/target flow rate indicator 340 may be set in any appropriate manner (e.g., in accordance with step 144 of the flow rate assessment protocol 140 of FIG. 4), while the actual/current flow rate indicator 342 will move along the flow rate meter 336 in response to changes in the flow rate. Other ways of graphically comparing the programmed/target flow rate with the corresponding actual/current flow rate may be utilized. A representative flow rate condition message 330$^{iii}$ may also be displayed on the progress screen 310$^{iii}$ (e.g., in accordance with step 162 of the flow rate assessment protocol 140 of FIG. 4).

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed:

1. A method of operation for a medical fluid delivery system, the method comprising the steps of:
   discharging medical fluid from said medical fluid delivery system in accordance with a phase of a fluid delivery protocol, wherein said phase is configured to deliver a programmed volume of said medical fluid at a programmed target flow rate; and
   displaying a first output, wherein said first output comprises a numerical comparison between a current flow rate of said discharging step and said target flow rate, wherein said numerical comparison comprises a single number, and wherein said discharging step is executed in an attempt to provide said target flow rate.

2. The method of claim 1, wherein said discharging step comprises discharging said medical fluid from a power injector.

3. The method of claim 1, wherein said discharging step comprises injecting said medical fluid into a fluid target.

4. The method of claim 3, wherein said fluid target comprises a patient.

5. The method of claim 1, wherein said displaying step comprises displaying said first output on at least one graphical user interface.

6. The method of claim 1, wherein said displaying step is executed only when said current flow rate differs from said target flow rate by more than a predetermined amount.

7. The method of claim 1, wherein said displaying step is continuously executed throughout said discharging step.

8. The method of claim 1, wherein said displaying step comprises expressing said current flow rate as a percentage of said target flow rate.

9. The method of claim 1, wherein said displaying step comprises displaying a differential between said current flow rate and said target flow rate.

10. The method of claim 1, wherein said displaying step comprises conveying information as to how said current flow rate differs from said target flow rate.

11. The method of claim 1, further comprising the step of:
   issuing a message that conveys that said discharging step is failing to comply with said target flow rate.

12. The method of claim 1, further comprising the step of:
   changing said discharging step if said current flow rate differs from said target flow rate in a predetermined manner.

13. The method of claim 12, further comprising the step of: inputting said predetermined manner.

14. The method of claim 12, wherein said discharging step uses a power injector, and wherein said method further comprises the step of:
   allowing operator input of said predetermined manner.

15. The method of claim 12, further comprising the step of:
   executing a first prompting step comprising prompting an entry of said predetermined manner on at least one graphical user interface.

16. The method of claim 15, further comprising the step of:
   executing a second prompting step comprising prompting an entry of said target flow rate on at least one graphical user interface.

17. The method of claim 1, further comprising the step of:
   terminating said discharging step if said current flow rate is less than a predetermined percentage of said target flow rate.

18. The method of claim 1, further comprising the step of:
   terminating said discharging step if said current flow rate is less than said target flow rate by a predetermined value.

19. A method of operation for a medical fluid delivery system, the method comprising the steps of:
   discharging medical fluid from said medical fluid delivery system in accordance with a phase of a fluid delivery protocol, wherein said phase is configured to deliver a programmed volume of said medical fluid at a programmed target flow rate; and
   displaying a first output, wherein said first output comprises a numerical comparison between a current flow rate of said discharging step and said target flow rate, wherein said discharging step is executed in an attempt to provide said target flow rate, and wherein said displaying step is executed only when said current flow rate differs from said target flow rate by more than a predetermined amount.

20. A method of operation for a medical fluid delivery system, the method comprising the steps of:
   discharging medical fluid from said medical fluid delivery system in accordance with a phase of a fluid delivery protocol, wherein said phase is configured to deliver a programmed volume of said medical fluid at a programmed target flow rate; and
   displaying a first output, wherein said first output comprises a numerical comparison between a current flow rate of said discharging step and said target flow rate, wherein said discharging step is executed in an attempt to provide said target flow rate, and wherein said displaying step comprises expressing said current flow rate as a percentage of said target flow rate.

21. A method of operation for a medical fluid delivery system, the method comprising the steps of:

discharging medical fluid from said medical fluid delivery system in accordance with a phase of a fluid delivery protocol, wherein said phase is configured to deliver a programmed volume of said medical fluid at a programmed target flow rate;

displaying a first output, wherein said first output comprises a numerical comparison between a current flow rate of said discharging step and said target flow rate, and wherein said discharging step is executed in an attempt to provide said target flow rate; and terminating said discharging step if said current flow rate is less than a predetermined percentage of said target flow rate.

* * * * *